United States Patent [19]

Wasserman et al.

[11] Patent Number: 4,929,751
[45] Date of Patent: May 29, 1990

[54] VINYL TRICARBONYL COMPOUNDS AND METHODS OF MAKING THE SAME

[75] Inventors: Harry H. Wasserman, New Haven, Conn.; Natesan Murugesan, Lawrenceville, N.J.; John H. Van Duzer, New Haven, Conn.

[73] Assignee: Yale University, New Haven, Conn.

[21] Appl. No.: 109,804

[22] Filed: Oct. 19, 1987

[51] Int. Cl.$^5$ .................... C07C 69/66; C07C 79/46; C07C 101/02; C07C 101/30; C07D 401/06; C07D 403/06; C07D 405/06; C07D 409/06; C07D 239/26; C07D 277/24; C07D 263/32; C07D 307/46

[52] U.S. Cl. .................... 560/174; 560/19; 560/20; 560/21; 560/22; 560/23; 560/38; 560/39; 560/42; 560/43; 560/45; 560/51; 560/53; 560/60; 560/116; 560/118; 560/122; 560/123; 560/124; 560/125; 560/126; 560/156; 560/170; 560/169; 544/296; 544/333; 544/335; 544/264; 544/277; 549/473; 549/494; 549/496; 549/498; 549/501; 549/59; 549/60; 549/76; 549/77; 549/79; 548/527; 548/517; 548/561; 548/562; 548/444; 548/236; 548/204; 548/336; 548/341; 548/342; 548/343; 548/181; 546/174; 546/267; 546/264; 546/272; 546/275; 546/276; 546/283; 546/278; 546/280; 546/281; 546/284; 546/330; 546/333; 546/335; 546/341; 546/342

[58] Field of Search .................... 560/19, 21, 60, 20, 560/22, 53, 116, 125, 126, 23; 549/473, 496, 501, 498; 548/517, 561, 336, 204; 546/264, 280, 276, 333, 283, 174; 544/277, 333

[56] References Cited

U.S. PATENT DOCUMENTS

| | | | |
|---|---|---|---|
| 2,158,724 | 5/1939 | Kilgore | 167/22 |
| 2,806,047 | 9/1957 | Bullock | 260/410.9 |
| 4,011,201 | 3/1977 | Ponticello | 260/65 |
| 4,245,122 | 1/1981 | Yoshida et al. | 568/397 |

OTHER PUBLICATIONS

Ban et al. Tetrahedron, vol. 39, pp. 3657–3668 (1983).
J. Am. Chem., (1989), 111, 371–372, "The Chem. of Vic. Tricarb., A Stable Vinyl Tricarb. Hydrate as a Di-and Trielectrophile", Wasserman.
J. Org. Chem., (1982), 47, 4955–4963, "Charge-Directed Conjugate Addition Reactions in the Preparation of Substitu. Methyl Ketones".

Primary Examiner—John M. Ford
Attorney, Agent, or Firm—Sprung, Horn, Kramer & Woods

[57] ABSTRACT

A vinyl tricarbonyl compound of the formula

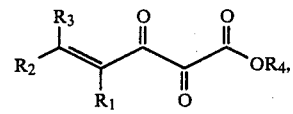

or its monohydrate of the formula

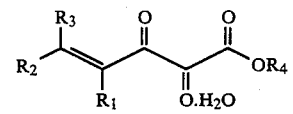

wherein $R_1$ is a hydrogen, halogen, unsubstituted or substituted $C_1$ to $C_{30}$ alkyl, unsubstituted or substituted aryl, arylalkyl, and cycloalkyl with 3 to 7 carbon atoms, $R_2$ is hydrogen, halogen, unsubstituted or substituted $C_1$ to $C_{30}$ alkyl, unsubstituted or substituted aryl, arylalkyl, cycloalkyl with 3 to 7 carbon atoms, cyano, nitro, or a heterocyclic, $R_3$ is hydrogen, halogen, unsubstituted or substituted $C_1$ to $C_{30}$ alkyl, unsubstituted or substituted aryl, arylalkyl, cycloalkyl with 3 to 7 carbon atoms, cyano, nitro, or a heterocyclic, and $R_4$ is unsubstituted or substituted $C_1$ to $C_{30}$ alkyl, unsubstituted or substituted aryl, arylalkyl, cycloalkyl are 3 to 7 carbon atoms. Such vinyl tricarbonyl compound is effective against tumor cells.

16 Claims, No Drawings

VINYL TRICARBONYL COMPOUNDS AND METHODS OF MAKING THE SAME

GOVERNMENT RIGHTS

This invention was made with United states government support under Grant 6M31350 from the NIH. The United States Government has certain rights in this invention.

BACKGROUND OF THE INVENTION

1. Field of the Invention

The present invention concerns vinyl tricarbonyl compounds and methods of making the same.

2. Background Information

A description of the formation of a keto-ester ylide precursor is found in Manning P. Cooke, Jr. and Diana L. Burman, "Charge-Directed Conjugate Addition Reactions in the Preparation of Substituted Methyl Ketones", *J. Org. Chem.*, 47, 4955–4963 (1982).

It is well known that alpha, beta-unsaturated carbonyl compounds are acceptors for certain nucleophiles as a result of Michael-like addition. Furthermore, 1,2,3-vicinyl tricarbonyls are known to be reactive as electrophiles by virtue of the strong electron-deficiency at the central carbonyl group.

SUMMARY OF THE INVENTION

It is an object of the present invention to produce vinyl tricarbonyl compounds which are novel functional groups aggregates which act as dielectrophiles, undergoing facile reaction with substances having dual nucleophilic capability.

It is another object of the invention to produce vinyl tricarbonyl aggregates combining both of the aforementioned types of electrophilic centers (i.e., alpha, beta-unsaturated carbonyl compounds and 1,2,3-vicinyl tricarbonyls) in one unit, rendering the resulting compound a potent dielectrophile so as to produce a compound which reacts with substituted amines to form a variety of heterocyclic systems of biological interest.

The above objects as well, as other objects and advantages, are satisfied by the present invention which concerns a vinyl tricarbonyl compound of the formula

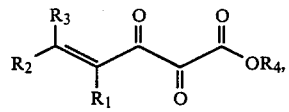

and/or its monohydrate of the formula,

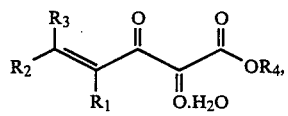

wherein
R$_1$ is hydrogen; halogen, e.g., fluorine, chlorine, bromine or iodine; cyano; nitro; unsubstituted or substituted C$_1$ to C$_{30}$ alkyl, preferably C$_2$ to C$_{20}$ alkyl; unsubstituted or substituted aryl, e.g., phenyl or naphthyl; arylalkyl, e.g., benzyl; and cycloalkyl with 3 to 7 carbon atoms, wherein the substituted alkyl and/or aryl is substituted by a substituent selected from the group consisting of halogen, e.g., fluorine, chlorine, bromine or iodine, alkoxy, nitro, cyano, amino and hydroxyl;

R$_2$ and R$_3$ are independently hydrogen; halogen, e.g., fluorine, chlorine, bromine or iodine; unsubstituted or substituted C$_1$ to C$_{30}$ alkyl, preferably C$_2$ to C$_{20}$ alkyl; cyano; nitro; aryl, e.g., phenyl or naphthyl; arylalkyl, e.g., benzyl; and cycloalkyl with 3 to 7 carbon atoms; wherein the substituted alkyl and/or aryl is substituted by a substituent selected from the group consisting of halogen, e.g., fluorine, chlorine, bromine, or iodine, alkoxy, nitro, cyano, amino, hydroxyl or a heterocyclic, e.g., furan, furfural, pyrrole, pyrrolidine, pyrroline, proline, pyrazole, pyridine, thiophene, imidazole, oxazole, thiazole, pyrimidine, purine, quinoline and carbazole;

R$_4$ is unsubstituted or substituted C$_1$ to C$_{30}$ alkyl, preferably C$_2$ to C$_{10}$ alkyl; unsubstituted or substituted aryl, e.g., phenyl or naphthyl; arylalkyl, e.g., benzyl; wherein the substituted alkyl and/or aryl is substituted by a substituent selected from the group consisting of halogen, e.g., fluorine, chlorine, bromine or iodine, alkoxy, nitro, cyano, amino and hydroxyl.

The present invention also concerns a method for producing vinyl tricarbonyl compounds. The method comprises reacting a compound of the formula

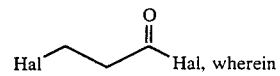

Hal is a halogen, e.g., fluorine, chlorine, iodine or bromine, with a compound of the formula

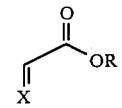

(wherein X is preferably Ph$_3$P) to form a compound of the formula

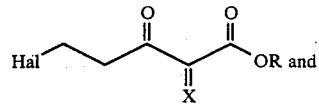

conducting oxidation, preferably using ozone, in the presence of a non-polar solvent, e.g., CH$_2$Cl$_2$, chloroform or dichloroethane, to form a compound of the formula

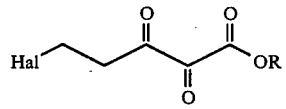

and thereafter reacting this compound with a weak, non-nucleophilic base, e.g., NaHCO$_3$ and a polar solvent, e.g., THF (tetrahydrofuran), dioxane or ether, to form

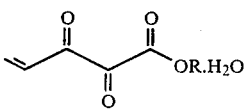

wherein

Hal is halogen, e.g., fluorine, chlorine, bromine or iodine and

R is unsubstituted or substituted $C_1$ to $C_{30}$ alkyl, preferably $C_2$ to $C_{10}$ alkyl; unsubstituted or substituted aryl, e.g., phenyl or naphthyl; arylalkyl, e.g., benzyl; wherein the substituted alkyl and/or aryl is substituted by a substituent selected from the group consisting of halogen, e.g., fluorine, chlorine, bromine or iodine, alkoxy, nitro, cyano, amino and hydroxyl.

DETAILED DESCRIPTION OF THE INVENTION

The vinyl tricarbonyl compounds of the present invention can be described as compounds containing a vinyl group conjugated to a vinyl tricarbonyl aggregate.

A preferred method of producing the vinyl tricarbonyl compounds according to the present invention is a so-called "Ylide Method" comprising the steps of (a) reacting a compound A of the formula

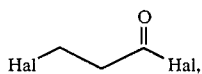

wherein

Hal is a halogen, e.g., fluorine, chlorine, bromine or iodine, with a compound B of the formula

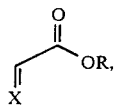

wherein

X is preferably $Ph_3P$, and can be $CHNR'_2$, $CHR'_2$, $N_2$, $NR'_3$, $S$, $SO$, $SR'_2$,

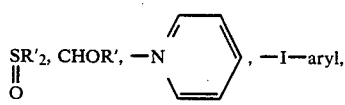

wherein R' is $C_1$ to $C_{30}$ alkyl, preferably $C_2$ to $C_{10}$ alkyl, unsubstituted or substituted aryl, e.g., phenyl or naphthyl; arylalkyl, e.g., benzyl; wherein the substituted alkyl and/or aryl is substituted by a substituent selected from the group consisting of halogen, e.g., fluorine, chlorine, bromine or iodine, alkoxy, nitro, cyano, amino and hydroxyl, R is unsubstituted or substituted $C_1$ to $C_{30}$ alkyl, preferably $C_2$ to $C_{10}$ alkyl; unsubstituted or substituted aryl, e.g., phenyl or naphthyl; arylalkyl, e.g., benzyl; wherein the substituted alkyl and/or aryl is substituted by a substituent selected from the group consisting of halogen, e.g., fluorine, chlorine, bromine or iodine, alkoxy, nitro, cyano, amino and hydroxyl, at a temperature of $-78°$ C. to $+25°$ C., preferably $-8°$ C. to $0°$ C., at a pressure of 3 atm to 0.5 atm, preferably 1 atm, for a time period of 2 hours to 36 hours, preferably 5 hours to 12 hours, wherein 0.45 moles to 0.5 moles of compound A, preferably 0.475 moles, are utilized per 1 mole of compound B, in the presence of a solvent, e.g., benzene, (b) reacting the product of step (a), namely compound C of the formula

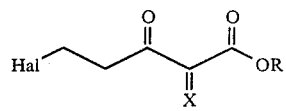

in the presence of an oxidizing agent, e.g., singlet oxygen, permanganate-periodate and in the case where $X=N_2$, hypochlorite (the preferred oxidizing agent is ozone), the oxidization being conducted at a temperature of $-78°$ C. to $0°$ C., preferably $-78°$ C. to $-40°$ C., at a pressure of 3 atm to 1 atm, preferably 1 atm, wherein 2 to 5 moles, preferably 2 to 2.5 moles of the oxidizing agent are utilized per mole of compound B in a non-polar solvent, e.g., $CH_2Cl_2$ and (c) reacting the product of step (b), namely compound D of the formula

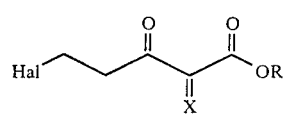

with a weak, non-nucleophilic base at a temperature of $0°$ C. to $25°$ C., preferably $20°$ C. to $25°$ C., at a pressure of 0.5 atm to 3 atm, preferably 1 atm and wherein 1 to 2 moles of the weak, non-nucleophilic base, e.g., $NaHCO_3$ or a tertiary amine, are utilized per mole of compound D, in the presence of a polar solvent, e.g., aqueous THF.

Another method for producing the vinyl tricarbonyl compounds according to the present invention is the so-called "Enamide Method" which is described in more detail hereinbelow in Example 2.

The vinyl tricarbonyl compounds of the present invention have the following advantages:

(1) they are effective against tumor cells;

(2) the compounds act as dielectrophiles, and, in some cases, as trielectrophiles, undergoing twofold or threefold attack by nucleophilic species;

(3) the use of the vinyl tricarbonyl compounds of the invention permits formation of pyrrolidones, pyrroles, indole derivatives and polycyclic aromatic systems by facile cyclization reactions taking place under mild conditions;

(4) the compounds of the invention permit the synthesis of a variety of products of biological interest including compounds in the erythrina alkaloid field, indole alkaloids and beta-lactams related to penicillin.

The invention will now be described with reference to the following non-limiting examples.

EXAMPLE 1

The vinyl tricarbonyl derivative (A) of the formula

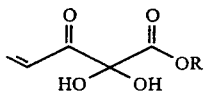

wherein
R=t-butyl (t-butyl 2,3-dioxo-pent-4-enoate hydrate) was prepared from the known ylide (B), of the formula

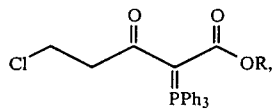

reported by Cooke et al, supra.

EXAMPLE 1a

Preparation of t-Butyl (Triphenylphosphoranylidene) Acetate

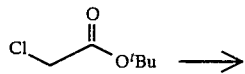

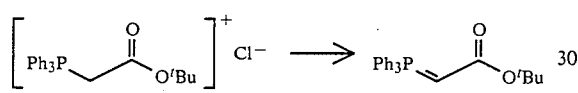

The following procedure according to Cooke et al supra was conducted:

A solution of triphenylphosphine (0.18 mol, 47.2 g) and t-butyl chloroacetate (0.16 mmol, 24.9 g) in benzene (200 ml) was heated at reflux for 48 hours. After cooling to room temperature, the resulting salt was collected by suction filtration and washed with cold benzene. Drying of the phosphonium salt in vacuo yielded t-butyl (triphenylphosphoranylidene) acetate as a white solid (55.1 g, 84%). To a solution of the crude salt (0.13 mol, 55.1 g) in water (1000 ml), cooled to 5° C., was added a solution of NaOH (0.15 mmol, 6.0 g) in water (200 ml) with vigorous stirring. There was an immediate formation of a white precipitate. After stirring the solution for five minutes at about 5° C., the precipitate was collected by suction filtration and washed well with cold water. This solid was dried in vacuo to yield the ylide as a white powder (47.7 g, 98%).

NMR: (60 MHz, CDCl$_3$): δ7.2–8.1 (m, 15H), 2.78 (br d, 1H), 1.26 (br s, 9H).

IR: (CHCl$_3$): 3000, 2980, 1605, 1435, 1360, 1162, 1102 cm$^{-1}$

EXAMPLE 1b

Preparation of t-Butyl 5-Chloro-3-oxo-2-(triphenylphosphoranylidene)-pentanoate

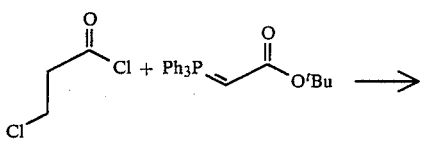

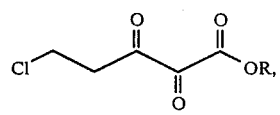

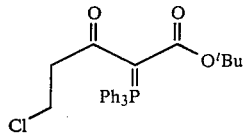

EXAMPLE 1c

Preparation of t-Butyl 2,3-Dioxo-pent-4-enoate Hydrate (A)

To a stirred solution of the ylide (20 mmol, 7.52 g) in dry benzene (50 ml), cooled to approximately 8° C., was added 3-chloropropanoyl chloride (10 mmol, 1.27 g) dropwise as a benzene solution (8 ml). After stirring for five minutes at approximately 8° C., the reaction mixture was heated to room temperature and stirred for an additional 30 minutes. Afterwards, ether (60 ml) was added and the precipitated phosphonium salt was removed by suction filtration. The filtrate was concentrated in vacuo to yield the crude beta-chloro acyl ylide as a thick, yellow oil (4.25 g), 91%). This material was used without further purification as attempted purification by chromatography or crystallization led to dehydrochlorination.

The reaction scheme for the synthesis is as follows:

Scheme I

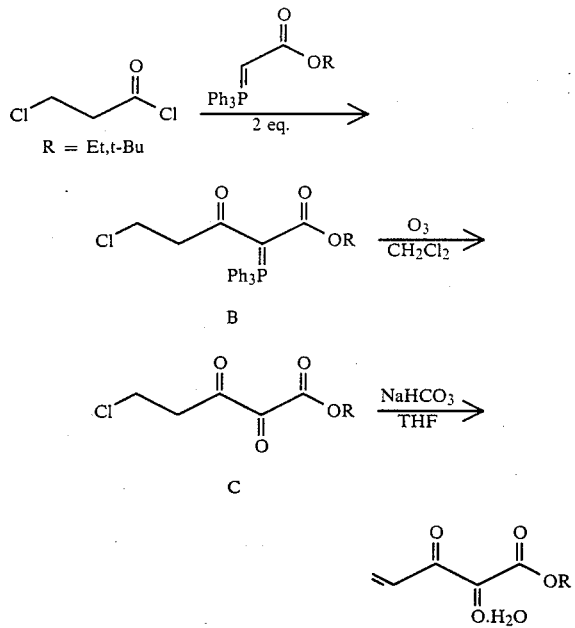

The procedure involved ozonolysis of (B) in methylene chloride to form the chlorodiketo ester (C) of the formula which was dehydrohalogenated directly without isolation using bicarbonate. The following are the experimental details:

A solution of the acyl ylide (B) (8.58 mmol, 4.0 g) in dry CH$_2$Cl$_2$ (85 ml) was cooled to −78° C. Ozone was passed through the yellow solution until an excess was indicated by the persistence of a dark green color. Excess ozone was removed from the reaction mixture by purging the solution with N$_2$ gas. After heating the solution to room temperature, the volatiles were removed in vacuo to give the chlorotricarbonyl as a dark yellow oil. Purification by flash chromatography (SiO$_2$, 5% EtOAc/CH$_2$Cl$_2$, 1:1) yielded the chloride as a light yellow oil.

The chlorotricarbonyl (7.26 mmol, 1.72 g) was dissolved in THF (50 ml) and saturated NaHCO$_3$ (5 ml). The resulting heterogenous solution was stirred vigorously for 9 hours. After diluting the reaction mixture with water (100 ml), the aqueous solution was extracted with EtOAc (2×100 ml). The combined extracts were dried (MgSO$_4$) and concentrated in vacuo to yield the vinyl tricarbonyl as a yellow oil. Purification by flash chromatography (SiO$_2$, CH$_2$Cl$_2$/EtoAc, 9:1) yielded compound (A) as a white solid, m.p. 58°–59° C. (1.20 g, 82%) (49% overall yield from the chloro ylide).

NMR: (90 MHz, CDCl$_3$): 6.63 (d, 2H, J=6), 6.03 (t, 1H, J=6), 5.10 (br 5, 2H), 1.45 (s, 9H).

MS: EI, M/Z (rel. %). 185 (42), 167 (18.5), 139 (5.4), 57 (100).

IR: (CCl$_4$): 3500, 1750, 1720, 1700, cm$^{-1}$.

Anal: Calculated for C$_9$H$_{14}$O$_5$: C, 53.46; H, 6.98 Found: C, 53.54; H, 6.98

For R=CH$_3$:
6.65 d, 1H (J=6)
6.63 d, 1H (J=5)
6.0 dd, 1H (J=6)
5.2 brd, variable
3.86 S, 3H For R=CH$_3$CH$_2$:
6.65 d, 1H (J=6)
6.63 d, 1H (J=5)
6.0 dd, 1H (J=6)
5.2 brd, variable
4.28 q, 2H (J=6)
1.27 tr, 3H (J=6)

EXAMPLE 2

An alternative procedure for the formation of compound (A) involved use of an enamine (D), in the following four step sequence.

Scheme II

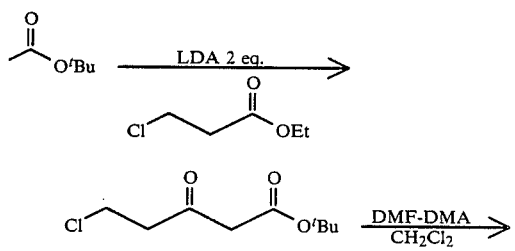

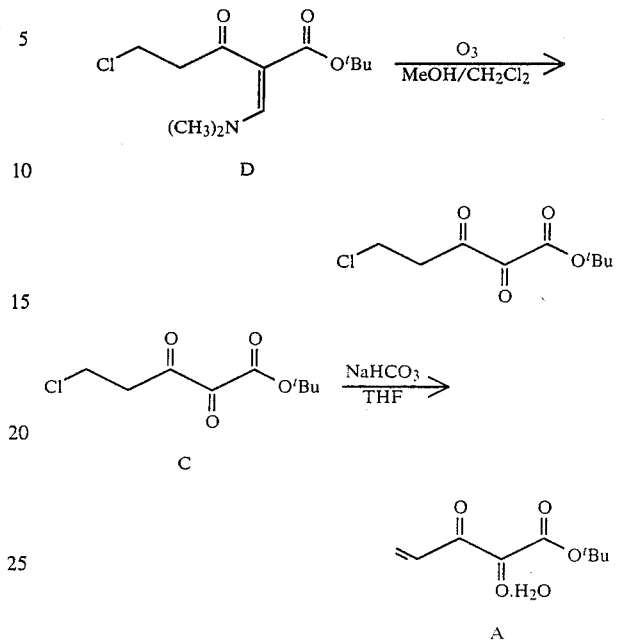

In the above scheme, DMF is dimethylformamide, DMA is dimethylacetal and LDA is lithium diisopropylamide.

EXAMPLE 2A

Preparation of t-Butyl 5-Chloro-3-oxopentanoate (see S. Ohta, A. Shimabayashi, S. Hatano and M. Okamoto, Synthesis, 715, (1983)).

To a stirred solution of diisoproply amine (20 mmol, 2.02 g, 3.05 ml) in dry THF (20 ml) at −78° C. was added n-butyllithium (20 mmol), 7.7 ml; 2.6M solution in hexanes. After stirring for 30 minutes, t-butyl acetate (22 mmol, 2.56 g) was added dropwise and the resulting mixture was stirred for 15 minutes. A solution of the lithium enolate of t-butyl acetate was subsequently added by cannula to a solution of ethyl 3-chloropropanoate (10 mmol, 1.37 g) in THF (25 ml) at −78° C. over 15 minutes. After stirring for an additional 15 minutes, the reaction was quenched by addition of glacial acetic acid (10 ml). After heating to room temperature, the reaction mixture was diluted with water (50 ml) and extracted with ether (150 ml). The ethereal extract was washed with 20% aqueous K$_2$CO$_3$ (2×100 ml), the organic phase was dried (MgSO$_4$) and then concentrated in vacuo. Purification of the resulting liquid by gradient flash chromatography (SiO$_2$, 1) 5% Et$_2$O/pentane, 2) 15% Et$_2$O/pentane) afforded t-butyl 5-chloro-3-oxopentanoate as a clear, colorless oil (4.08 g, 99%).

NMR: (90 MHz, CDCl$_3$) 3.73 (t, 2H, J=6), 3.38 (5, 2H), 3.02 (t, 2H, J=6), 1.49 (s, 9H).

EXAMPLE 2B

Preparation of t-Butyl 2-dimethylaminomethylene-3-oxo-5-chloro-pentanoate (D)

To a solution of the beta-ketoester (19.9 mmol, 4.10 g) in CH$_2$Cl$_2$ (20 ml) was added N,N-dimethylformamide dimethyl acetal (37.5 mmol, 4.0 ml) in one portion at 0° C. After stirring at 0° C. for five hours, the volatiles were removed in vacuo to leave the enamine as a thick oil which crystallized to a solid (m.p. 50°–51° C.). Purification by flash chromatography (SiO$_2$, 3:2 pentane/Et$_2$O, 3.2) yielded t-butyl 2-dimethylaminomethylen-3-oxo-5-chloro-pentanoate as a yellow oil (4.40 g, 85%).

NMR: (90 MHz, CDCl$_3$) 7.68 (S, 1H), 3,83 (t, 2H, J=7), 3.16 (t, 2H, J=7), 3.08 (Br 5, 6H), 1.55 (S, 9H).

MS: EI, M/Z (Rel. %) 263 (2.9), 261 (8.1), 188 (41.7), 170 (86.4), 142 (100).

IR: (CCl$_4$): 1740, 1995, 1640, 1580 cm$^{-1}$.

EXAMPLE 2C

Preparation of t-Butyl 2,3-Dioxo-pent-4-enoate Hydrate (A)

The enamine (D) (12.1 mmol, 3.2 g) was dissolved in 4:1 CH$_2$Cl$_2$:MeOH (120 ml) and cooled to $-78°$ C. Ozone was passed through the solution until excess O$_3$ was indicated by the persistence of a light blue color. After purging the reaction mixture with N$_2$ gas, dimethyl sulfide (5 ml) was added and the reaction was allowed to warm to room temperature over three hours. Subsequently, the volatiles were removed in vacuo and the resulting oil was purified by flash chromatography (SiO$_2$, 9:1 CH$_2$Cl$_2$/EtOAc, 9:1) to give the chlorotricarbonyl as a light yellow oil (1.72 g, 60%). The chlorotricarbonyl (7.26 mmol, 1.72 g) was dehydrohalogenated as previously described to yield the vinyl tricarbonyl derivative (A) in a 49% yield from the enamine.

EXAMPLES 3 TO 7

Other representative derivatives corresponding to A have been prepared by the same procedure.

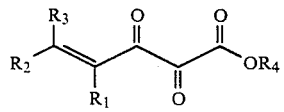

cl EXAMPLE 3
R$_1$=R$_2$=R$_3$=H; R$_4$=t-butyl

EXAMPLE 4

R$_1$=R$_2$=R$_3$=H; R$_4$=methyl

EXAMPLE 5

R$_1$=R$_2$=R$_3$=H; R$_4$=ethyl

EXAMPLE 6

R$_1$=R$_2$=CH$_3$; R$_3$=H; R$_4$=t-butyl

EXAMPLE 7

R$_1$=R$_2$=R$_3$=H; R$_4$=-nitrobenzyl

EXAMPLE 8

Activity of Inventive Compounds Against Tumor Cells t-Butyl 2,3-dioxo-pent-4-enoate hydrate (A) was contacted with various cell lines as indicated on Table 1 hereinbelow in the column designated as "CELL" or "TUMOR". It was found that this compound was particularly effective against ovarian cell line OVCAR-5. The results of such tests are in Table 1.

As described below, the data in Table 1 serve to display the testing results on disease category selectivity in a bar graph format. Bars projecting to the right of the reference (vertical line of asterisks) indicate greater than average sensitivity to the test compound. Each bar represents one power of ten in sensitivity, so that the results for OVCAR-5 (ovarian tumor) indicate a remarkable (10$^{18}$) increase in sensitivity over the reference test.

Table 1 reports and illustrates the results obtained by testing t-butyl 2,3-dioxo-pent-4-enoate hydrate. The concentration of this compound found to inhibit the growth of each cell line listed under "CELL" by 50% is reported under "LOG(IC50)" as the logarithm of the concentration. The units of concentration are either molarity in which case an "M" is shown in parentheses next to the LOG(IC50) label, or micrograms per ml, in which case a "W" (for weight) is shown in parenthesis. The cell line names are grouped by disease type and the disease type names are listed on the far left.

The graph on the right depicts the data on the left in a format called a "MEAN GRAPH" which is designed to aid in the identification of differential growth inhibition. Differential growth inhibition means that a particular cell line or a given category of cell lines, e.g., a group of colon cell lines, responds at a significantly lower concentration of test compound than do other cell lines or groups of cell lines. The interest in using this concept of differential growth inhibition as a criterion of activity in the screening system is to encourage the discovery of new types of anticancer agents having greater tissue specificity than cancer chemotherapeutic agents in use today.

The idea for the Mean Graph resulted from trying to detect differential growth inhibition in a bar graph format. Experimentation led to a graph centered at the arithmetic mean (ML) of the logarithm of the IC50'a of all the cell line responses measured for a compound. The Mean Graph is constructed around a vertical reference (indicating ML) by projecting bars to the right or to the left. The direction depends on whether a specific cell line shows more or less sensitivity than average to the test compound. The lengths of the bars are proportional to the differences between the logarithms of the specific cell line IC50's and the overall mean value ML. These lengths represent differences in logarithms which are equivalent to the ratios of the specific IC50's to the geometric mean of all the IC50's. Therefore, a useful property of the Mean Graph format is the ability to compare patterns derived from IC50's measured in different units, e.g, micrograms per ml and molarity. The units cancel in the division process.

Differential growth inhibition is depicted as a bar projecting some distance to the right of ML. A bar projecting three log units to the right of ML, for example, would reflect a cellular sensitivity 1000 times greater than ML. While any degree of sensitivity greater than ML might theoretically be considered differential growth inhibition, in practice one must consider the experimental error in the measurement and at what point the degree of differential growth inhibition becomes meaningful in biological terms. The three values listed a the bottom of the graph provide the value of ML as "AVE LOG(IC50)", the greatest difference from ML as "DELTA" and the difference between the least sensitive cell line and the most sensitive cell line as the "RANGE".

TABLE 1

| CELL | | DIFFERENCE |
|---|---|---|
| * LEUK | LOGIC50(M) | MEAN LOG IC50s |

TABLE 1-continued

| | | |
|---|---|---|
| CCRF-CE | −5.1 | *]]]]]]]] |
| K562 | −4 | [[ * |
| * PS | | |
| P388 | −4 | [ * |
| * RESISTL | | |
| P388/AD | −3.9 | [[ * |
| * NSCLC | | |
| H522 | −4.8 | *]]]]]] |
| SK-MES1 | >−4.6 | *]]] |
| H125 | −4.3 | *] |
| H358 | −3.8 | [[[ * |
| H23 | −4.3 | *]] |
| H460 | >−3.6 | [[[[[ * |
| H520 | −4 | [[ * |
| H322 | −4.3 | *]] |
| A549 | >−3.6 | [[[[[[ * |
| EKV-X | −3.7 | [[[[[ * |
| * SCLC | | |
| H82 | −4.4 | *]]] |
| H524 | −4.4 | *]]] |
| DMS114 | −3.9 | [[[ * |
| H69 | −4 | [ * |
| H146 | −3.9 | [[ * |
| * COLON | | |
| SW620 | −4.2 | *] |
| LOVO | −4 | [ * |
| DLD-1 | −4.4 | *]]] |
| HCC2998 | >−4.3 | *]] |
| * BREAST | | |
| MCF-7 | −4 | [ * |
| * RESISTB | | |
| MCF-7/A | −4 | [ * |
| * CNS | | |
| TE-671 | −3.9 | [[[ * |
| SNB-19 | −4 | [[ * |
| SNB-44 | −4 | [[ * |
| SNB-75 | −4.1 | * |
| * MELANOMA | | |
| SK-MEL5 | −4.2 | *] |
| RPMI-79 | −4.1 | * |
| MALME-3 | −4 | [ * |
| LOX | −4 | [[ * |
| SK-MEL2 | −4.1 | * |
| * OVARIAN | | |
| A2780 | −4.2 | *] |
| OVCAR-8 | −3.9 | [[ * |
| OVCAR-3 | −4 | [ * |
| OVCAR-5 | −5.9 | *]]]]]]]]]]]]]] |
| OVCAR-4 | −3.6 | [[[[[ * |
| * RENAL | | |
| CAKI-1 | −4.3 | *]] |
| A704 | −4.3 | *]] |
| UO-31 | >−3.6 | [[[[[ * |
| *AV TC50 | −4.13 | * |
| *DELTA | 1.8 | ***************** |
| *RANGE | 2.3 | ***** ***************** |

DISEASE CATEGORY SELECTIVITY
SORTED BY DIFFERENCE FROM MEAN
TOTAL CELL LINES USED= 42
MEAN OF ALL LOGIC50'S= −4

| TEST | MEAN CAT | DIFF CAT | CELL BEST | IC50 | # IN CAT. |
|---|---|---|---|---|---|
| LEUK | −4.5 | −0.4 | CCRF-CE | −5.1 | 2 |
| OVARIAN | −4.3 | −0.2 | OVCAR-5 | −5.9 | 5 |
| COLON | −4.2 | −0.1 | DLD-1 | −4.4 | 4 |
| NSCLC | −4.1 | 0 | H522 | −4.8 | 10 |
| SCLC | −4.1 | 0 | H82 | −4.4 | 5 |
| MEL | −4.1 | 0 | SK-MEL5 | −4.2 | 5 |
| RENAL | −4.1 | 0.1 | A704 | −4.3 | 3 |
| RESISTB | −4 | 0.1 | MCF-7/A | −4 | 1 |
| PS | −4 | 0.1 | P388 | −4 | 1 |
| BREAST | −4 | 0.1 | MCF-7 | −4 | 1 |
| CNS | −4 | 0.2 | SNB-75 | −4.1 | 4 |
| RESISTL | −3.9 | 0.2 | P388/AD | −3.9 | 1 |

Legend
LEUK = leukemia
NSCLC = non-small cell lung cancer
SCLC = small cell lung cancer
MEL = melanoma
RESISTB = resistant breast cancer
CNS = central nervous system
RESISTL = resistant lung cancer

| TYPE | TUMOR | NUM ATT | ID C | USED | IC-50 MEAN | DEV. | USED | IC-90 MEAN | DEV |
|---|---|---|---|---|---|---|---|---|---|
| LUN | H23 | 2 | 1 | 1 | 5.27E-05 | | 1 | 1.97E-04 | |
| | H522 | 2 | 1 | 1 | 1.43E-05 | | 0 | | |
| | A549 | 2 | 2 | 0 | | | 0 | | |
| | EKV-X | 2 | 2 | 2 | 2.26E-04 | 1.34E-05 | 0 | | |
| | H125 | 2 | 2 | 2 | 7.33E-05 | 3.50E-05 | 0 | | |
| | H520 | 2 | 1 | 1 | 1.05E-04 | | 0 | | |
| | SK-MES-1 | 2 | 2 | 1 | 5.45E-08 | | 0 | | |
| | H322 | 2 | 1 | 1 | 4.87E-05 | | 1 | 2.46E-04 | |
| | H358 | 2 | 2 | 2 | 1.55E-04 | 7.21E-06 | 0 | | |
| | H460 | 2 | 1 | 0 | | | 0 | | |
| SCL | H69 | 2 | 1 | 1 | 9.55E-05 | | 1 | 2.69E-04 | |
| | H146 | 2 | 1 | 1 | 1.24E-04 | | 0 | | |
| | H82 | 2 | 2 | 2 | 3.67E-05 | 7.21E-07 | 2 | 1.72E-04 | 2.23E-06 |
| | H524 | 2 | 1 | 1 | 4.08E-05 | | 1 | 1.89E-04 | |
| | DMS114 | 2 | 1 | 1 | 1.41E-04 | | 1 | 2.64E-04 | |
| COL | HT29 | 2 | 1 | 0 | | | 0 | | |
| | HCC-2998 | 2 | 1 | 1 | 5.20E-05 | | 0 | | |
| | LOVO | 2 | 1 | 1 | 9.66E-05 | | 1 | 2.62E-04 | |
| | SW620 | 2 | 2 | 2 | 5.80E-05 | 9.54E-06 | 1 | 2.34E-04 | |
| | DLD-1 | 2 | 1 | 1 | 3.84E-05 | | 1 | 1.87E-04 | |
| BRE | MCF-7 | 2 | 1 | 1 | 9.81E-05 | | 1 | 2.32E-04 | |
| | MCF-7/ADR | 2 | 1 | 1 | 9.60E-05 | | 0 | | |
| OVA | OVCAR-3 | 2 | 2 | 1 | 9.66E-05 | | 1 | 2.70E-04 | |
| | OVCAR-4 | 2 | 1 | 0 | | | 0 | | |
| | OVCAR-5 | 2 | 2 | 2 | 2.01E-06 | 1.01E-06 | 0 | | |
| | OVCAR-8 | 2 | 2 | 2 | 1.14E-04 | 1.41E-06 | 1 | 2.63E-04 | |
| | A2780 | 2 | 1 | 1 | 7.03E-05 | | 1 | 2.49E-04 | |
| LEU | P388 | 2 | 2 | 2 | 1.14E-04 | 2.75E-05 | 2 | 2.48E-04 | 1.34E-05 |
| | P388/ADR | 2 | 1 | 1 | 1.18E-04 | | 1 | 2.44E-04 | |
| | CCRF-CEM | 2 | 1 | 1 | 8.05E-06 | | 0 | | |
| | K562 | 2 | 2 | 2 | 9.03E-05 | 1.18E-05 | 2 | 2.25E-04 | 7.21E-06 |
| | MOLT-4 | 2 | 1 | 0 | | | 1 | 2.44E-04 | |
| | HL-60 | 2 | 1 | 0 | | | 0 | | |
| KID | UO-31 | 2 | 2 | 0 | | | 0 | | |
| | SN-12KI | 2 | 0 | 0 | | | 0 | | |

-continued

| TYPE | TUMOR | NUM ATT | ID C | USED | IC-50 MEAN | DEV. | USED | IC-90 MEAN | DEV |
|------|-------|---------|------|------|-----------|------|------|-----------|-----|
|  | A498 | 2 | 0 | 0 |  |  | 0 |  |  |
|  | A704 | 2 | 2 | 1 | 4.66E-05 |  | 1 | 2.29E-04 |  |
|  | CAKI-1 | 2 | 2 | 2 | 6.49E-05 | 2.19E-05 | 2 | 2.02E-04 | 3.39E-05 |
| MEL | LOX | 2 | 1 | 1 | 1.02E-04 |  | 1 | 2.58E-04 |  |
|  | MALME-3M | 2 | 2 | 2 | 7.88E-05 | 1.58E-05 | 2 | 1.80E-04 | 6.71E-05 |
|  | RPMI-7951 | 2 | 2 | 2 | 7.67E-05 | 1.54E-05 | 2 | 1.78E-04 | 6.57E-05 |
|  | SK-MEL2 | 2 | 2 | 2 | 7.35E-05 | 8.98E-06 | 2 | 1.74E-04 | 5.79E-05 |
|  | SK-MEL5 | 2 | 2 | 2 | 7.42E-05 | 2.29E-05 | 2 | 2.22E-04 | 3.04E-05 |
| CNS | SNB-19 | 2 | 2 | 2 | 9.52E-05 | 1.37E-05 | 2 | 2.43E-04 | 1.14E-05 |
|  | SNB-44 | 2 | 2 | 2 | 9.40E-05 | 1.40E-05 | 2 | 2.35E-04 | 1.14E-05 |
|  | SNB-75 | 2 | 1 | 1 | 8.15E-05 |  | 1 | 2.31E-04 |  |
|  | U-251 | 2 | 0 | 0 |  |  | 0 |  |  |
|  | TE-671 | 2 | 2 | 2 | 1.14E-04 | 2.84E-05 | 1 | 2.31E-04 |  |
| NSC | MEAN |  |  |  | 7.91E-05 |  |  |  |  |

Legend
LUN = lung
SCL = small cell lung cancer
COL = colon
BRE = breast
OVA = ovarian
KID = kidney
MEL = melanoma
CNS = central nervous system

| TUMOR | STATUS | ATT | TUMOR | STATUS | ATT | TUMOR | STATUS | ATT |
|-------|--------|-----|-------|--------|-----|-------|--------|-----|
| H 23 | C | 2 | MCF-7 | C | 2 | RPMI-7951 | C | 2 |
| H 522 | C | 2 | MCF-7/ADR | C | 2 | SK-MEL 2 | C | 2 |
| A 549 | > | 2 | OVCAR-3 | C | 2 | SK-MEL 5 | C | 2 |
| EKV-X | C | 2 | OVCAR-4 | C | 2 | SNB-19 | C | 2 |
| H 125 | C | 2 | OVCAR-5 | C | 2 | SNB-44 | C | 2 |
| H 520 | C | 2 | OVCAR-8 | C | 2 | SNB-75 | C | 2 |
| SK-MES-1 | C | 2 | A 2780 | C | 2 | U-251 | Q | 2 |
| H 322 | C | 2 | P 388 | C | 2 | TE-671 | C | 2 |
| H 358 | C | 2 | P 388/ADR | C | 2 |  |  |  |
| H 460 | > | 2 | CCRF-CEM | C | 2 |  |  |  |
| H 69 | C | 2 | K 562 | C | 2 |  |  |  |
| H 146 | C | 2 | MOLT-4 | R | 2 |  |  |  |
| H 82 | C | 2 | HL-60 | R | 2 |  |  |  |
| H 524 | C | 2 | UO-31 | > | 2 |  |  |  |
| DMS 114 | C | 2 | SN-12 KI | Q | 2 |  |  |  |
| HT 29 | > | 2 | A 498 | Q | 2 |  |  |  |
| HCC-2998 | C | 2 | A 704 | C | 2 |  |  |  |
| LOVO | C | 2 | CAKI-1 | C | 2 |  |  |  |
| SW 620 | C | 2 | LOX | C | 2 |  |  |  |
| DLD-1 | C | 2 | MALME-3 M | C | 2 |  |  |  | legend
">" means a true IC-50 not obtained, rather the IC-50 is greater than value shown
"Q" and "R" not acceptable tests
"C" good tests It will be appreciated that the instant specification and claims are set forth by way of illustration and not limitation, and that various modifications and changes may be made without departing from the spirit and scope of the present invention.

What is claimed is:

1. A vinyl tricarbonyl of the formula

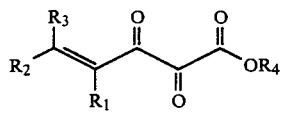

or its monohydrate of the formula

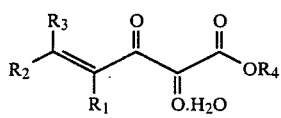

wherein $R_1$ is hydrogen, halogen, unsubstituted $C_1$ to $C_{30}$ alkyl, $C_1$ to $C_{30}$ alkyl substituted by a substituent selected from the group consisting of halogen, alkoxy, nitro, cyano, amino and hydroxyl, unsubstituted phenyl, unsubstituted naphthyl, substituted phenyl and substituted naphthyl, said substituted phenyl and said substituted naphthyl being substituted by a substituent selected from the group consisting of halogen, alkoxy, nitro, cyano, amino and hydroxyl, benzyl, and cycloalkyl with 3 to 7 carbon atoms, $R_2$ is hydrogen, halogen, unsubstituted $C_1$ to $C_{30}$ alkyl, $C_1$ to $C_{30}$ alkyl substituted by a substituent selected from the group consisting of halogen, alkoxy, nitro, cyano, amino and hydroxyl, unsubstituted phenyl, unsubstituted naphthyl, substituted phenyl, substituted naphthyl, said substituted phenyl and said substituted naphthyl being substituted by a substituent selected from the group consisting of halogen, alkoxy, nitro, cyano, amino and hydroxyl, benzyl, cycloalkyl with 3 to 7 carbon atoms, cyano, nitro or a heterocyclic selected from the group consisting of furan, furfural, pyrrole, pyridine, thiophene, imidazole, oxazole, thiazole, pyrimidine, purine, guinoline and carbazole, $R_3$ is hydrogen, halogen, unsubstituted $C_1$ to $C_{30}$ alkyl, $C_1$ to $C_{30}$ alkyl substituted by a substituent selected from the group consisting of halogen, alkoxy, nitro, cyano, amino and hydroxyl, unsubstituted phenyl, unsubstituted naphthyl, substituted phenyl, substituted naphthyl, said substituted phenyl and said substituted naphthyl being substituted by a substituent selected from the group consisting of halogen, alkoxy, nitro, cyano, amino and hydroxyl, benzyl, cycloalkyl with 3 to 7 carbon atoms, cyano, nitro, or a heterocyclic selected from the group consisting of furan, furfural, pyrrole, pyridine, thiophene, imidazole, oxazole, thiazole, pyrimidine, purine, quinoline and carbazole and $R_4$ is unsubstituted $C_1$ to $C_{30}$ alkyl, $C_1$ to $C_{30}$ alkyl substituted by a substituent selected from the group consisting of halogen, alkoxy, nitro, cyano, amino and hydroxyl, unsubstituted phenyl, unsubstituted naphthyl, substituted phenyl, substituted naphthyl, said substituted phenyl and said substituted naphthyl being substituted by a substituent selected from the group consisting of halogen, alkoxy, nitro, cyano, amino and hydroxyl, benzyl or cycloalkyl with 3 to 7 carbon atoms.

2. A vinyl tricarbonyl according to claim 1, wherein $R_1$, $R_2$ and $R_3$ are hydrogen and $R_4$ is t-butyl.

3. A vinyl tricarbonyl according to claim 1, wherein $R_1$, $R_2$ and $R_3$ are hydrogen and $R_4$ is $CH_3$.

4. A vinyl tricarbonyl according to claim 1, wherein $R_1$, $R_2$ and $R_3$ are hydrogen and $R_4$ is $CH_3CH_2$.

5. A vinyl tricarbonyl according to claim 1, wherein $R_1$, $R_2$ $R_3$ are hydrogen and $R_4$ is nitrobenzyl.

6. A vinyl tricarbonyl according to claim 1, wherein the halogen substituent for said phenyl and said naphthyl is selected from the group consisting of fluorine, chlorine, bromine and iodine.

7. A vinyl tricarbonyl according to claim 1, wherein said alkyl has 2 to 20 carbon atoms.

8. A vinyl tricarbonyl according to claim 1, wherein $R_1$ is a halogen selected from the group consisting of fluorine, chlorine, bromine and iodine.

9. A vinyl tricarbonyl according to claim 1, wherein $R_2$ is a halogen selected from the group consisting of fluorine, chlorine, bromine and iodine.

10. A vinyl tricarbonyl according to claim 1, wherein $R_3$ is a halogen selected from the group consisting of fluorine, chlorine, bromine and iodine.

11. A process for making a vinyl tricarbonyl of the formula

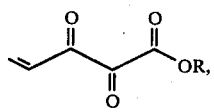

comprising
(a) reacting a compound A of the formula

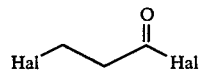

, wherein Hal is a halogen, with a compound B of the formula

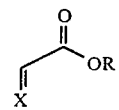

to form a compound C of the formula

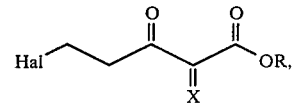

(b) subjecting compound C to oxidation in the presence of a non-polar solvent to form a compound D of the formula

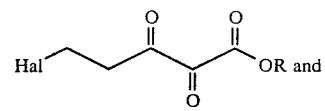

and thereafter (c) reacting compound D with a weak, non-nucleophilic base and a polar solvent, wherein R is unsubstituted $C_1$ to $C_{30}$ alkyl, $C_1$ to $C_{30}$ alkyl substituted by a substituent selected from the group consisting of halogen, alkoxy, nitro, cyano, amino and hydroxyl, unsubstituted phenyl, unsubstituted naphthyl, substituted phenyl, substituted naphthyl, said substituted phenyl and said substituted naphthyl being substituted by a substituent selected from the group consisting of halogen, alkoxy, nitro, cyano, amino and hydroxyl, benzyl, cycloalkyl with 3 to 7 carbon atoms and wherein X is selected from the group consisting of $Ph_3P$, $CHNR'_2$, $CHR'_2N_2$, $NR'_3$, S, SO, $SR'_2$,

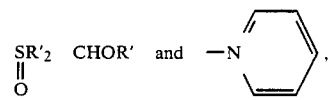

wherein $R^1$ is unsubstituted $C_1$ to $C_{30}$ alkyl, $C_1$ to $C_{30}$ alkyl substituted by a substituent selected from the group consisting of halogen, alkoxy, nitro, cyano, amino and hydroxyl, unsubstituted, phenyl, unsubstituted naphthyl, substituted phenyl, substituted naphthyl, said substituted phenyl and said substituted naphthyl being substituted by a substituent selected from the group consisting of halogen, alkoxy, nitro, cyano, amino and hydroxyl, benzyl or cycloalkyl with 3 to 7 carbon atoms.

12. A process according to claim 11, wherein said oxidation is conducted in the presence of an oxidation agent selected from the group consisting of ozone, singlet oxygen and permanganate-periodate.

13. A process according to claim 11, wherein the weak, non-nucleophilic base is $NaHCO_3$.

14. A process according to claim 11, wherein the polar solvent is aqueous THF.

15. A process according to claim 11, wherein the non-polar solvent is $CH_2Cl_2$.

16. A process according to claim 11, wherein X is $Ph_3P$.

* * * * *